United States Patent [19]

Reynolds

[11] Patent Number: 4,995,812
[45] Date of Patent: Feb. 26, 1991

[54] METHOD OF OBTAINING USABLE HYDROCOLLOID IMPRESSION MATERIAL

[76] Inventor: Fred W. Reynolds, 1516 W. 1st St., #110, San Pedro, Calif. 90732

[21] Appl. No.: 430,296

[22] Filed: Nov. 2, 1989

[51] Int. Cl.⁵ ............................................. A61C 9/00
[52] U.S. Cl. ...................................... 433/214; 264/16
[58] Field of Search .................... 433/32, 214; 264/16, 264/25, 26, 27

[56] References Cited

U.S. PATENT DOCUMENTS

| | | | |
|---|---|---|---|
| 1,977,580 | 10/1934 | Grier | 264/16 |
| 2,315,748 | 4/1943 | Thompson | 433/32 |
| 3,635,630 | 1/1972 | Greene | 425/175 |

FOREIGN PATENT DOCUMENTS 1052227  11/1983  U.S.S.R. ............................ 433/32

Primary Examiner—Gene Mancene
Assistant Examiner—Adriene B. Lepiane
Attorney, Agent, or Firm—Jack C. Munro

[57] ABSTRACT

A method of obtaining hydrocolloid impression material to be used in conjunction with making dental impressions where a quantity of the hydrocolloid impression material in solid form is cut into a mass of small parts. This mass of small parts is then heated within a microwave oven until the mass is liquefied and achieves a homogeneous consistency. The liquid mass is then poured into a tray and tempered and then utilized to make a desired dental impression.

4 Claims, 1 Drawing Sheet

METHOD OF OBTAINING USABLE HYDROCOLLOID IMPRESSION MATERIAL

BACKGROUND OF THE INVENTION

The field of this invention relates to dentistry and more particularly to a novel method of liquefying a hydrocolloid material which is utilized to make dental impressions.

In the field of dentistry, it is exceedingly common to make impressions of portions of the mouth of a human being. These impressions are then utilized to make dental appliances such as bridges, crowns, caps, etc. In the making of these dental impressions, it is common to utilize either a liquid rubber material which includes a hardening agent or a hydrocolloid. Hydrocolloid is composed of natural ingredients and in essence is a water based gelatin. The impression taken by the hydrocolloid is not only quite accurate, but it is less expensive than rubber impression material.

Normally, hydrocolloid is packaged within plastic tubes. When it is desired to use a quantity of hydrocolloid, a tube is placed within boiling water and boiled for an extended length of time. A typical extended length of time may be twenty to thirty minutes. If hydrocolloid could be melted without boiling water in a shorter length of time, then the dentist need not melt and store hydrocolloid ahead of time. The dentist need only melt what is needed when needed.

SUMMARY OF THE INVENTION

The method of the present invention would have the hydrocolloid impression material packaged differently from the normal. The prior art method of dealing with hydrocolloid is a solid encased in a plastic tube. Melting is done in boiling water with the hydrocolloid in the tube and with the tube lid on tight. The method of this invention requires that the hydrocolloid material be cut into a mass of small particles. This mass of small particles could be formed by grating, granulization, or merely cutting. A desired amount of these small particles is then placed within a vessel which is then located within a microwave type of oven. This hydrocolloid material is then heated for a sufficient length of time which would be generally no more than five minutes until the hydrocolloid material has assumed a homogeneous liquefied state. This hydrocolloid material is then removed from the microwave oven and poured into a dental tray. This hydrocolloid material is then tempered to a temperature which will permit the hydrocolloid to be inserted within the mouth of the human being without causing injury to the tissues of the mouth. This tempered hydrocolloid is used to take impressions. Then the tray, containing the hydrocolloid, is removed from the mouth and utilized in the constructing of a dental appliance.

The primary objective of the present invention is to provide for a method of melting hydrocolloid into a usable form in a very short period of time.

Another objective of the present invention is to use an ordinary microwave type of oven as the heating source for the hydrocolloid thereby eliminating the need to manufacture and purchase a separate heating device.

DETAILED DESCRIPTION OF THE SHOWN EMBODIMENT

Figure 1:
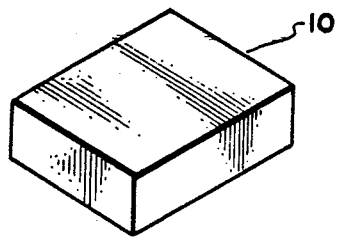
FIG. 1 depicts a block of hydrocolloid material.
Figure 2:
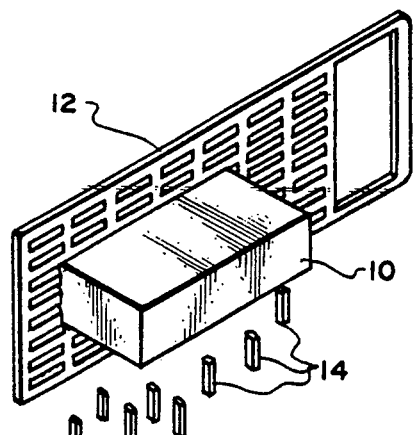
FIG. 2 depicts the grating of the block into a mass of small particles.
Figure 3:
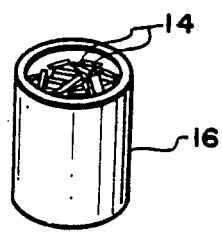
FIG. 3 shows placing of the particles into a small vessel.
Figure 4:
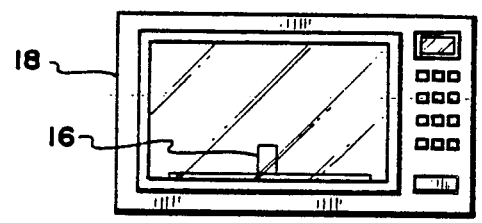
FIG. 4 shows placing the vessel within a microwave type of oven.
Figure 5:
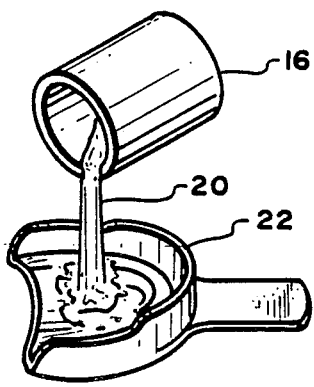
FIG. 5 is a view depicting pouring of the liquid hydrocolloid from the vessel into a dental tray.
Figure 6:
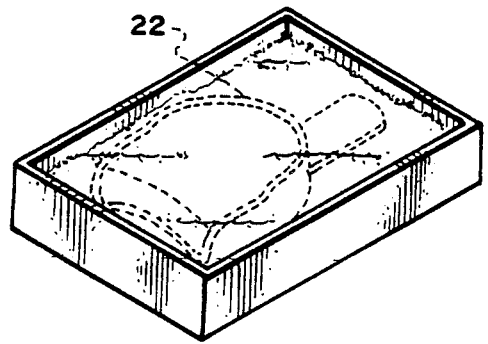
FIG. 6 is a view depicting tempering of the tray to an acceptable temperature level.
Figure 7:
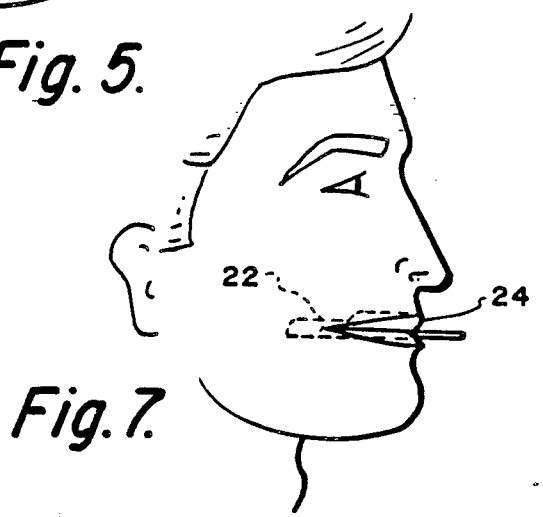
FIG. 7 shows placing of the tray within a dental patient's mouth.
Figure 8:
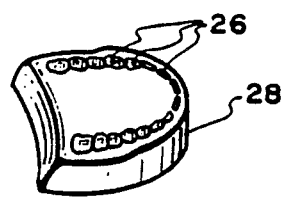
FIG. 8 shows the tray removed from the patient's mouth which is then to be utilized to manufacture a dental appliance.

Referring particularly to the drawing, there is shown block 10 of hydrocolloid material. A desirable material would be what is manufactured by Gingi-Pak either the 500-Type, the 510-Type or the 530-Type. The 530-Type is heavier in body than the 510-Type. The 500-Type is heavier in body than the 530-Type.

The block 10 of hydrocolloid material is grated by grater 12 into a mass of small size particles 14. A quantity of these particles 14 is then placed within a vessel 16. This vessel 16 is then located within a microwave oven 18.

The grating process produces pieces of hydrocolloid approximately two millimeters by four millimeters by ten millimeters. However, it is to be understood that smaller sized particles could be utilized, or larger sized particles could be utilized. Also, grating is not the only process that would be satisfactory. It is just that it has been found to be important to maximize the surface area of the material that is being heated. The grating process does an effective job of maximizing this surface area.

Using enough grated hydrocolloid that when melted would fill a medium size upper dental tray, typical heating within the microwave would be for ninety-seconds at a medium power setting and then an additional forty-five seconds at a higher power setting. Total time within the microwave oven would be approximately two minutes and fifteen seconds. Within this period of time the hydrocolloid was completely melted with an end temperature of approximately one hundred seventy-five degrees Fahrenheit. This would be for the lighter type of hydrocolloid.

If the hydrocolloid is of the heavier type, a slight increase in time will be required and also the ending temperature might be a little bit higher such as approximately one hundred ninety degrees Fahrenheit. If the hydrocolloid is formed into pieces that are larger than grated pieces, satisfactory liquefying of the hydrocolloid can be obtained by using a medium temperature range setting with the microwave oven and extending the time period for the melting process. Possibly four to five minutes would be required in this particular situation and an ending temperature of approximately one hundred fifty degrees Fahrenheit would result. This lower end temperature is desirable.

After heating within the microwave 18, the vessel 16 is removed from the microwave 18. The liquid hydrocolloid 20 within the vessel 16 is then to be poured into a desirably shaped tray 22. At this particular time, the liquid hydrocolloid 20 is at too high of a temperature to be placed within the mouth of a human being. Therefore, the liquid hydrocolloid 20 would have to be lowered in temperature but still remain melted and deformable. This lowering of the temperature of the tray 22 can be accomplished by merely leaving of the loaded tray 22 in air for three to four minutes or placing the loaded tray 22 within a shallow dish which is filled with hot tap water (this water can be any temperature from one hundred twenty-five degrees Fahrenheit to one hundred thirty-five degrees Fahrenheit) for two or three minutes. When the hydrocolloid approaches approximately one hundred twenty to one hundred thirty degrees Fahrenheit, it is now ready to be used to form an impression. The human mouth is comfortable with higher temperatures than the fingers or hand are comfortable with. The tray and material may feel hot, but the mouth will not notice any discomfort at all.

The tray 22 and the now tempered hydrocolloid is to be placed within the mouth 24 of a human being. The tray 22 is pressed to place at a particular location in the mouth forming an impression within the tempered hydrocolloid. The hydrocolloid remains in the mouth until solidified and then the tray 22 is removed with this impression 26 within this solidified hydrocolloid 28 now to be used to manufacture a custom dental appliance for that particular patient.

What is claimed is:

1. A method of obtaining usable hydrocolloid impression material comprising the steps of:

acquiring a solid block of hydrocolloid at around room temperature;
   cutting said block into a mass of individual small parts;
   subjecting said parts to microwave energy for a predetermined length of time until said parts are completely melted and intermixed forming a homogeneous liquid mass at an elevated temperature;
   pouring said liquid mass into a tray;
   tempering said liquid mass to a temperature which would be acceptable to the tissue within the mouth of a human being;
   inserting said tempered mass and said tray into the mouth of the human being and applying said tempered mass against a particular area of the mouth to make an impression of the area of the mouth within said tempered mass; and
   utilizing of said impression to construct a dental appliance.

2. The method as defined in claim 1 wherein;
   said cutting step is accomplished by grating of said block.

3. The method as defined in claim 2 wherein:
   the grated said small parts are each of the approximate size of two millimeters by four millimeters by ten millimeters.

4. The method as defined in claim 1 wherein:
   said elevated temperature is at least one hundred fifty degrees Fahrenheit.

* * * * *